(12) United States Patent
Birky (10) Patent No.: US 10,816,524 B2
(45) Date of Patent: Oct. 27, 2020

(54) METHOD FOR CALCULATING AMOUNT OF AMMONIA IN GAS SAMPLE

(71) Applicant: Caterpillar Inc., Peoria, IL (US)

(72) Inventor: Zachary S. Birky, Washington, IL (US)

(73) Assignee: Caterpillar Inc., Peoria, IL (US)

( * ) Notice: Subject to any disclaimer, the term of this patent is extended or adjusted under 35 U.S.C. 154(b) by 300 days.

(21) Appl. No.: 15/922,131

(22) Filed: Mar. 15, 2018

(65) Prior Publication Data

US 2019/0285599 A1    Sep. 19, 2019

(51) Int. Cl.
  *G01N 33/00*    (2006.01)

(52) U.S. Cl.
  CPC ....... *G01N 33/0054* (2013.01); *G01N 33/005* (2013.01); *G01N 33/0006* (2013.01); *G01N 33/0024* (2013.01)

(58) Field of Classification Search
  CPC ............. G01N 33/0006; G01N 33/005; G01N 33/0054; G01N 33/0024
  USPC ...................... 436/113, 144, 181; 422/83, 93
  See application file for complete search history.

(56) References Cited

U.S. PATENT DOCUMENTS

| 3,232,851 A | 2/1966 | Haber et al. |
| 3,366,456 A | 1/1968 | Andreatch et al. |
| 3,545,931 A * | 12/1970 | McKinley, Jr. ........ G01N 31/00 436/113 |
| 3,977,836 A * | 8/1976 | Matsuda .............. G01N 31/005 436/113 |
| 5,965,801 A | 10/1999 | Layzell et al. |
| 7,763,154 B2 | 7/2010 | Schumann et al. |
| 2006/0039826 A1* | 2/2006 | Nakatani .............. G01N 31/005 422/68.1 |
| 2006/0237333 A1 | 10/2006 | Planje |
| 2016/0258333 A1* | 9/2016 | Birky ..................... F01N 3/208 |

FOREIGN PATENT DOCUMENTS

| JP | 3151711 | * | 7/2009 |
| WO | 9106852 | | 5/1991 |

* cited by examiner

*Primary Examiner* — Maureen Wallenhorst
(74) *Attorney, Agent, or Firm* — Hibshman Claim Construction PLLC (57) ABSTRACT

A method for calculating an amount of ammonia present in a gas sample is provided. The method includes receiving a first gas sample by a hydrogen analyzer. The first gas sample contains ammonia. The method also includes receiving a second gas sample by the hydrogen analyzer. The second gas sample is formed by eliminating ammonia from the gas sample. The method further includes measuring, by the hydrogen analyzer, an output signal for each of the first and second gas samples. The method includes calculating the amount of ammonia present in the gas sample based on the measured output signal for each of the first and second gas samples and a hydrogen error correction value.

20 Claims, 4 Drawing Sheets

METHOD FOR CALCULATING AMOUNT OF AMMONIA IN GAS SAMPLE

TECHNICAL FIELD

The present disclosure relates to a method for calculating an amount of ammonia present in a gas sample.

BACKGROUND

During a heat treatment process, such as gas nitriding, a concentration of ammonia and hydrogen present in a gas sample is analyzed to control the heat treatment process. Accordingly, ammonia analyzers and hydrogen analyzers are used to analyze the concentration of ammonia and hydrogen in the gas sample. In order to closely monitor the heat treatment process, frequent water burette readings must be taken or expensive ammonia analyzers are required for analyzing the concentration of ammonia in the gas sample. Using the water burette for analyzing the concentration of ammonia is generally suitable in lab environments. Further, using expensive ammonia analyzers available in the market increase an overall cost of the heat treatment process.

Additionally, when hydrogen analyzers are used to analyze the concentration of hydrogen in the gas sample, the ammonia in a balance of nitrogen changes the thermal conductivity of the gas sample, thereby creating error in the hydrogen analyzer. It should be further noted that presence of other gases, such as hydrogen, carbon monoxide, carbon dioxide, oxygen, etc., also affect the error in a similar manner as the presence of ammonia in the gas sample. Thus, a value of the concentration of hydrogen received from the hydrogen analyzer is unreliable.

U.S. Pat. No. 5,965,801 describes a method and apparatus for rapidly measuring nitrogenase activity of a nitrogen fixing plant growing in a medium in a non-porous container. Gas containing hydrogen is sampled at the surface of the medium at a rate approximately equal to the rate of hydrogen diffusion from the medium, and the sample is passed to a hydrogen sensor where it is measured and nitrogenase activity is determined therefrom.

SUMMARY OF THE DISCLOSURE

In one aspect of the present disclosure, a method for calculating an amount of ammonia present in a gas sample is provided. The method includes receiving a first gas sample by a hydrogen analyzer. The first gas sample contains ammonia. The method also includes receiving a second gas sample by the hydrogen analyzer. The second gas sample is formed by eliminating ammonia from the gas sample. The method further includes measuring, by the hydrogen analyzer, an output signal for each of the first and second gas samples. The method includes calculating the amount of ammonia present in the gas sample based on the measured output signals for the first and second gas samples and a hydrogen error correction value.

In another aspect of the present disclosure, a method for calculating an amount of ammonia present in a gas sample is provided. The method includes receiving, by a hydrogen analyzer, a first gas sample through a first gas flow path. The first gas sample contains ammonia. The method also includes receiving, by the hydrogen analyzer, a second gas sample through a second gas flow path. The second gas sample is formed by eliminating ammonia from the gas sample using a gas treatment on it mounted in the second gas flow path. The method further includes measuring, by the hydrogen analyzer, an output signal for each of the first and second gas samples. The method includes receiving, by a control module, the measured output signals for each of the first and second gas samples from the hydrogen analyzer. The method also includes calculating, by the control module, the amount of ammonia present in the gas sample based on the measured output signals for each of the first and second gas samples and a hydrogen error correction value.

In yet another aspect of the present disclosure, a system for calculating an amount of ammonia present in a gas sample is provided. The system includes a hydrogen analyzer in selective fluid communication with a first gas flow path and a second gas flow path. The hydrogen analyzer is configured to receive a first gas sample from the first gas flow path and a second gas sample from the second gas flow path. The first gas sample contains ammonia and the second gas sample is formed by eliminating ammonia from the gas sample using a gas treatment unit mounted in the second gas flow path. The hydrogen analyzer is also configured to measure an output signal for each of the first and second gas samples. The system also includes a control module communicably coupled with the hydrogen analyzer. The control module is configured to receive the measured output signals for each of the first and second gas samples from the hydrogen analyzer. The control module is also configured to calculate the amount of ammonia present in the gas sample based on the measured output signals for the first and second gas samples and a hydrogen error correction value.

Other features and aspects of this disclosure will be apparent from the following description and the accompanying drawings.

DETAILED DESCRIPTION

Wherever possible, the same reference numbers will be used throughout the drawings to refer to the same or the like parts. Also, corresponding or similar reference numbers will be used throughout the drawings to refer to the same or corresponding parts.

Figure 1:
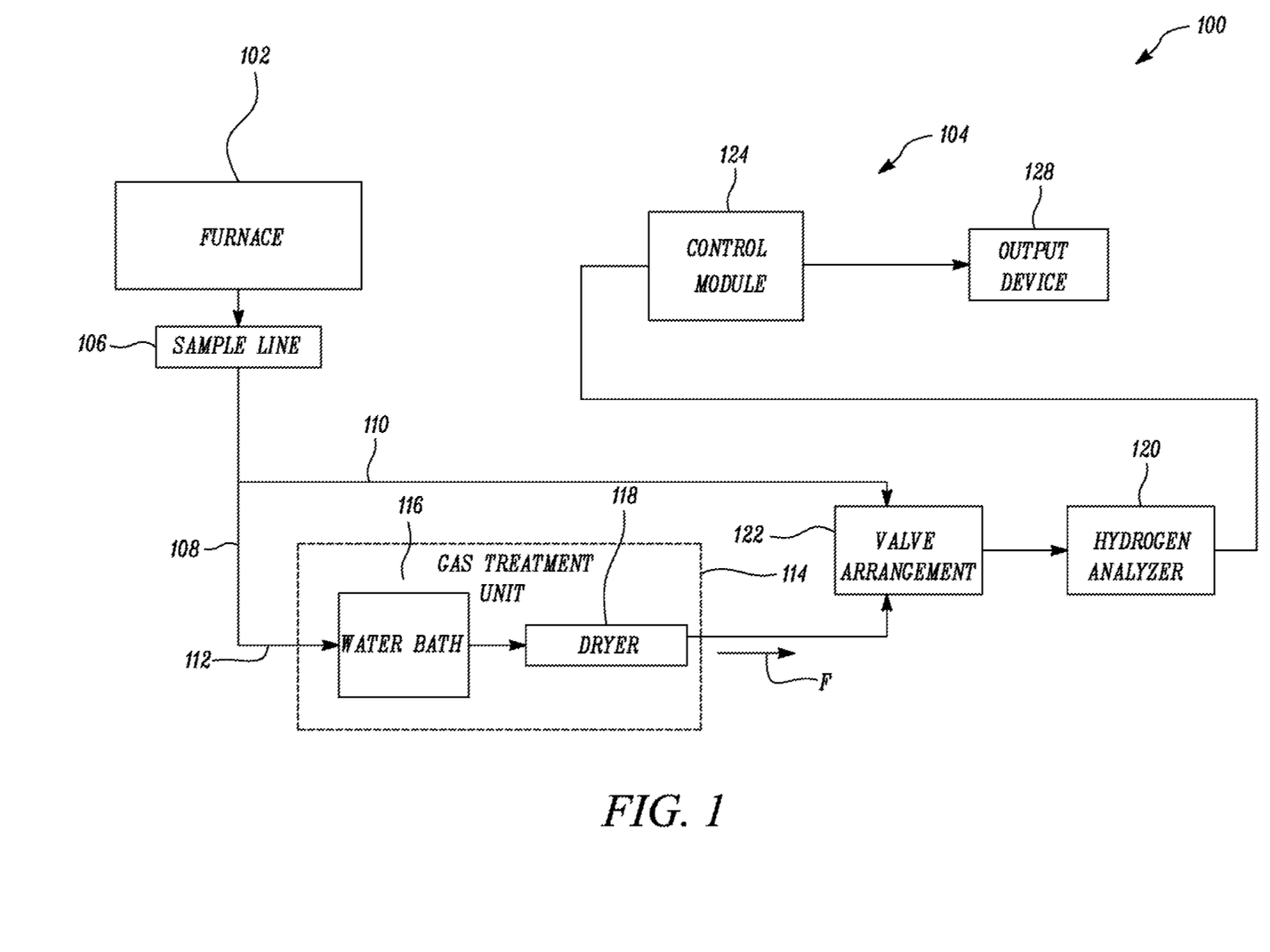
FIG. 1 is a block diagram of an exemplary set-up for performing a heat treatment process, wherein the set-up includes an ammonia measurement system, according to one embodiment of the present disclosure.

FIG. 1 is a block diagram of an exemplary set-up for performing a heat treatment process, according to one embodiment of the present disclosure. In the illustrated example, the set-up 100 is used to perform a gas nitriding process on a work piece (not shown). The gas nitriding process is performed in a furnace 102 that holds the work piece therein. In one example, a gas containing ammonia is used to perform the gas nitriding process on the work piece.

Further, in order to closely monitor and control the gas nitriding process, the set-up 100 includes an ammonia measurement system 104, hereinafter referred to as the system 104. The system 104 is used to calculate an amount of ammonia present in the gas that is used in the gas nitriding process. The system 104 includes a sample line 106 in fluid communication with the furnace 102. The sample line 106 receives a gas sample from the furnace 102. The gas sample is a portion of the gas that is used in the gas nitriding process. The system 104 analyzes the gas sample to calculate the amount of ammonia present in the gas that is used in the gas nitriding process. The sample line 106 is adapted to receive and/or hold the gas sample therein. In some examples, the sample line 106 may embody a reservoir that is replenished with fresh gas samples at different instances of time during a gas nitriding process, without any limitations.

Further, the system 104 includes a flow path 108 in fluid communication with the sample line 106. The gas sample from the sample line 106 is received by the flow path 108. In one example, the flow path 108 may be omitted and a first gas flow path 110 and a second gas flow path 112 may be provided in direct fluid communication with the sample line 106, without any limitations. In yet another example, the sample line 106 may be replaced by a valve (not shown) that allows fluid communication between the furnace 102 and the flow path 108, such that the flow path 108 may receive the gas sample based on system requirements, without limiting the scope of the present disclosure.

Further, the flow path 108 is in fluid communication with the first and second gas flow paths 110, 112. Each of the first and second gas flow paths 110, 112 receive some amount of the gas sample from the sample line 106 through the flow path 108. More particularly, a first gas sample that contains ammonia flows through the first gas flow path 110 and a second gas sample flows through the second gas flow path 112, such that the second gas sample is formed by eliminating ammonia from the gas sample.

The flow path 108, the first gas flow path 110, and the second gas flow path 112 may be embodied as tubes or pipes, without any limitations. For example, the flow path 108, the first gas flow path 110, and the second gas flow path 112 may be made of a flexible material, such as a hose. Further, the flow path 108, the first gas flow path 110, and the second gas flow path 112 may be made of steel pipes, without any limitations.

As shown in the accompanying figures, the system 104 includes a gas treatment unit 114. The gas treatment unit 114 is mounted in the second gas flow path 108. In order to form the second gas sample, the gas treatment unit 114 treats the gas sample to eliminate the ammonia from the gas sample. It should be noted that the second gas sample exiting the gas treatment unit 114 is substantially dry and ammonia-free.

In one example, the gas treatment unit 114 includes a water bath 116 and a dryer 118. The dryer 118 is mounted downstream of the water bath 116 along a flow direction "F" of the second gas sample. As ammonia is soluble in water, the water bath 116 eliminates the ammonia from the gas sample such that the resulting second gas sample is ammonia free and only contains hydrogen and nitrogen. The second gas sample is then passed through the dryer 118. The dryer 118 is used to eliminate any water vapor that is present in the second gas sample.

Alternatively, the gas treatment unit 114 includes a catalyst (not shown) that eliminates the ammonia from the gas sample in order to form the second gas sample. In one example, the gas treatment unit 114 may include a high temperature catalyst for eliminating the ammonia from the gas sample, without any limitations.

The system 104 also includes a hydrogen analyzer 120. The hydrogen analyzer 120 may include any known in the art hydrogen analyzer that is capable of measuring output signals for any given gas sample, without limiting the scope of the present disclosure. The hydrogen analyzer 120 is in selective fluid communication with the first and second gas flow paths 110, 112. Thus, the hydrogen analyzer 120 receives the first gas sample from the first gas flow path 110 and the second gas sample from the second gas flow path 112. The hydrogen analyzer 120 alternately receives each of the first and second gas samples form the first and second gas flow paths 110, 112, respectively. More particularly, a valve arrangement 122 provides selective fluid communication between the hydrogen analyzer 120 and the first and second gas flow paths 110, 112, respectively, so that the hydrogen analyzer 120 can alternately receive the first and second gas samples from the first and second gas flow paths 110, 112, respectively. In one example, the valve arrangement 122 includes a 3-way valve. Alternatively, the valve arrangement 122 may include any other type of valve that allows the hydrogen analyzer 120 to selectively receive the first and second gas samples from the first and second gas flow paths 110, 112, respectively.

In the illustrated example, the hydrogen analyzer 120 measures an output signal for each of the first and second gas samples. The term "output signal" referred to herein is indicative of a concentration of hydrogen and other gases present in the respective first and second gas samples. When the hydrogen analyzer 120 receives the first gas sample for analysis, the output signal for the first gas sample includes a true concentration of hydrogen in the first gas sample and also a false hydrogen concentration that is detected by the hydrogen analyzer 120 in a presence of ammonia. The false hydrogen concentration detected in the presence of ammonia is an error that causes the hydrogen analyzer 120 to give a faulty reading for the concentration of hydrogen present in the first gas sample.

Further, since the second gas sample only includes hydrogen and nitrogen, the output signal measured by the hydrogen analyzer 120 only gives a true concentration of hydrogen present in the second gas sample without any false hydrogen concentration. Accordingly, the concentration of hydrogen detected in the first gas sample is always greater than a concentration of hydrogen calculated by a control module 124 for the second gas sample.

It should be further noted that an amount of hydrogen for the second gas sample may be higher compared to an amount of hydrogen that is present in the first gas sample, since a composition of the second gas sample changes after elimination of the ammonia present in the gas sample. For example, if the gas sample includes 50% of ammonia, 10% of hydrogen, and 40% of nitrogen, and when the gas sample is treated in the water bath to eliminate the ammonia, the new concentration of the second gas sample would include 20% of hydrogen and 80% of nitrogen. Accordingly, the hydrogen analyzer 120 measures an output signal of 20% of hydrogen in the second gas sample. Further, the control module 124 that is communicably coupled with the hydrogen analyzer 120 processes the measured output signal to determine the actual amount of hydrogen that is present in the gas sample. Thus, the control module 124 processes an output signal of 20% of hydrogen in order to calculate the actual amount of hydrogen present in the gas sample, which is equal to 10% of hydrogen in this example.

Alternatively, if the catalyst is used to break down the ammonia, the new concentration of the second gas sample would include 56.7% of hydrogen and 43.3% of nitrogen. Accordingly, the hydrogen analyzer 120 measures an output signal of 56.7% of hydrogen in the second gas sample. Again, the control module 124 processes the measured output signal to determine the actual amount of hydrogen that is present in the gas sample. Thus, the control module 124 processes an output signal of 56.7% of hydrogen in order to calculate the actual amount of hydrogen present in the gas sample, which is equal to 10% of hydrogen in this example.

Thus, the control module 124 also determines the actual amount of hydrogen that is present in the gas sample, based on the measured output signal for the second gas sample. More particularly, as the measured output signal for the second gas sample does not include any false hydrogen concentration, a value obtained by processing the measured output signal for the second gas sample corresponds to the actual amount of hydrogen present in the gas sample.

Further, the control module 124 receives the measured output signals for the first and second gas samples from the hydrogen analyzer 120. The control module 124 also calculates the amount of ammonia present in the gas sample. The amount of ammonia is calculated based on the measured output signals for the first and second gas samples and a hydrogen error correction value. More particularly, the amount of ammonia is calculated based on a difference between the measured output signal for the first gas sample including the error and the value obtained from the control module 124 on processing the measured output signal for the second gas sample that is received from the hydrogen analyzer 120, and the hydrogen error correction value, it should be noted that the amount of ammonia present in the gas sample is a product of difference between the measured output signal for the first gas sample and the value obtained by processing the measured output signal for the second gas sample received from the hydrogen analyzer 120, and the hydrogen error correction value.

A value of the hydrogen error correction value mentioned above varies with the amount of ammonia and other gases that are present in the gas sample. The hydrogen error correction value is generally calculated in advance by a personnel in-charge of the gas nitriding process. In some examples, the hydrogen error correction value is stored in a separate database (not shown) that is communicably coupled with the control module 124 such that the control module 124 can retrieve the hydrogen error correction value from the database as and when required. Alternatively, the hydrogen error correction value may be stored in a memory of the control module 124 and can be accessed as and when required.

Figure 2:
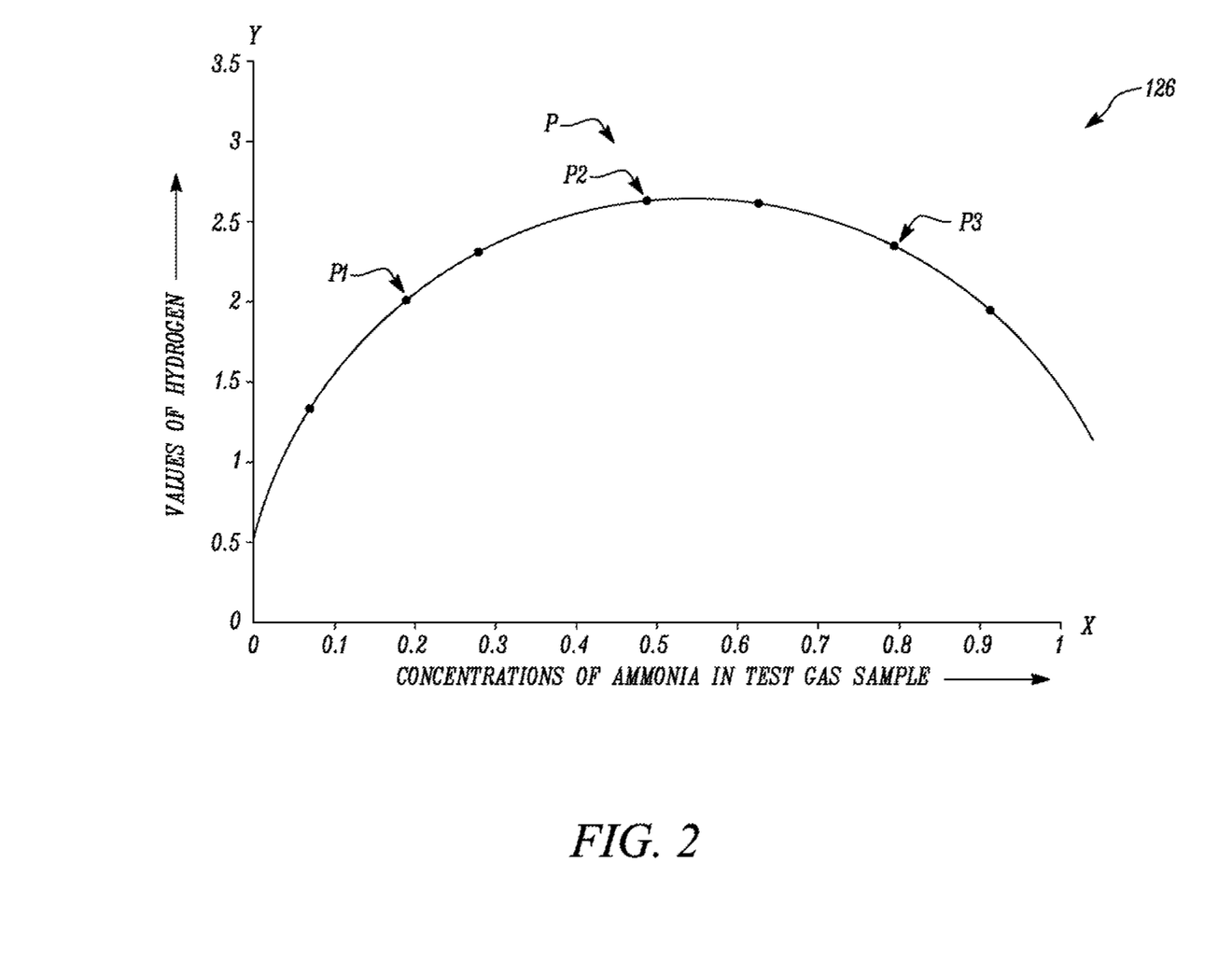
FIG. 2 is a plot for calculating a hydrogen error correction value by analyzing a test gas sample, according to one embodiment of the present disclosure.

Referring now to FIG. 2, a plot 126 for calculating the hydrogen error correction value is illustrated. It should be noted that the plot 126 may be manually generated by the personnel or may be generated using a computer, without any limitations. Further, the hydrogen error correction value is calculated based on an output signal from a hydrogen analyzer with a test gas sample at different concentrations of ammonia. More particularly, the personnel measures a concentration of ammonia present in the test gas sample using a water burette when the furnace 102 is in a shut-down mode. The concentration of ammonia present in the test gas sample is marked on an axis "X" of the plot 126. It should be noted that in the illustrated example, the test gas sample is the gas that is used in the gas nitriding process.

Further, the personnel measures an output signal for the test gas sample corresponding to the respective know concentration of ammonia. The term "output signal" referred to herein is indicative of the concentration of hydrogen and other gases present in the test gas sample. The output signal may be measured using the hydrogen analyzer 120 or a different hydrogen analyzer, without any limitations. The measured output signal for the test gas sample is marked on an axis "Y" of the plot 126.

Further, a set of coordinates "P" are generated by plotting the measured output signals for the test gas sample corresponding to the known concentration of ammonia in the test gas sample. The set of coordinates "P" include a number of coordinates "P1", "P2", "P3", and so on. The coordinates "P1", "P2", "P3" represent the measured output signals for the test gas sample corresponding to the respective known concentration of ammonia. For example, at 20% (0.2 volume fraction) of ammonia, the output signal approximately measures 2.5% of hydrogen. Similarly, at 50% (0.5 volume fraction) of ammonia, the output signal approximately measures 3.25% of hydrogen, at 80% (0.8 volume fraction) of ammonia; the output signal approximately measures 2.75% of hydrogen, and so on. It should be noted that only 3 coordinates are illustrated in the accompanying figure for exemplary purposes, however, a total number of coordinates in the set of coordinates "P" may vary without any limitations.

It should be further noted that a presence of gases, such as nitrogen, hydrogen, carbon monoxide, carbon dioxide, oxygen, etc., may also affect the output signals tier the test gas sample in a similar manner as the presence of ammonia. For example, the measured output signal for the test gas sample may be highest when the test gas sample only contains ammonia in a balance of nitrogen, and the measured output signal for the test gas sample may decrease as hydrogen is added to the test gas sample. In one example, where the test gas sample contains 50% (0.5 volume fraction) of ammonia in a balance of nitrogen, an output signal for the test gas sample indicates an error of 3.2%. Further, if the test gas sample contains 50% (0.5 volume fraction) of ammonia and 10% of hydrogen in a balance of nitrogen, the output signal for the test gas sample may be approximately equal to 12%, indicating an error of 2%.

Further, a curve "C" is created that passes through the number of coordinates "P1", "P2", "P3". The curve "C" is generally a parabolic curve. The hydrogen error correction value is calculated by solving an equation of the curve "C". In some examples, the equation of the curve "C" is generally a second order quadratic equation or a third order quadratic equation that is mathematically solved to calculate the hydrogen error correction value at a particular concentration of ammonia in the test gas sample.

The system 104 also includes an output device 128. The output device 128 is communicably coupled to the control module 124, and receives control signals therefrom. The output device 128 receives a value of the amount of ammonia and/or the actual amount of hydrogen present in the gas sample from the control module 124. Further, the output device 128 notifies a person in-charge of the gas nitriding process regarding the amount of ammonia and/or the actual amount of hydrogen present in the gas sample.

The output device 128 may include any known visual device for example, a monitor, a touchscreen, and so on that displays a visual feedback regarding the amount of ammonia and/or the actual amount of hydrogen present in the gas sample, without any limitations. Alternatively, the output device 128 may include any known audio device, such as a speaker, that provides an audio feedback regarding the amount of ammonia and/or the actual amount of hydrogen present in the gas sample, without any limitations.

Further, the control module 124 may embody a single microprocessor or multiple microprocessors. Numerous commercially available microprocessors can be configured to perform the functions of the control module 124. The control module 124 may include all the components required to run an application such as, for example, a memory, a secondary storage device, and a processor, such as a central processing unit or any other means known in the art. Various other known circuits may be associated with the control module 124, including power supply circuitry, signal-conditioning circuitry, solenoid driver circuitry, communication circuitry, and other appropriate circuitry.

INDUSTRIAL APPLICABILITY

Figure 3:
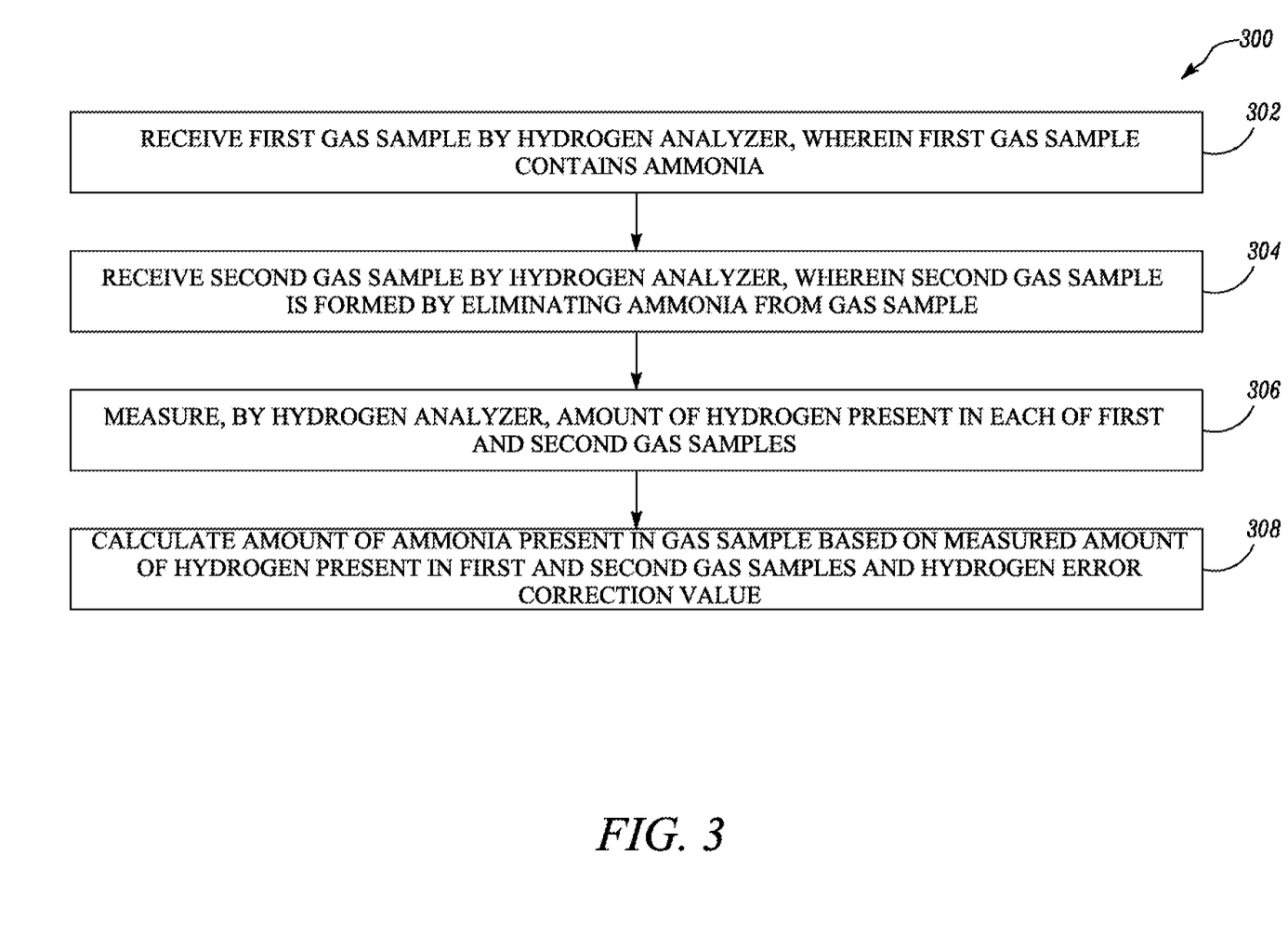
FIG. 3 is a flowchart for a method of calculating an amount of ammonia present in a gas sample.
Figure 4:
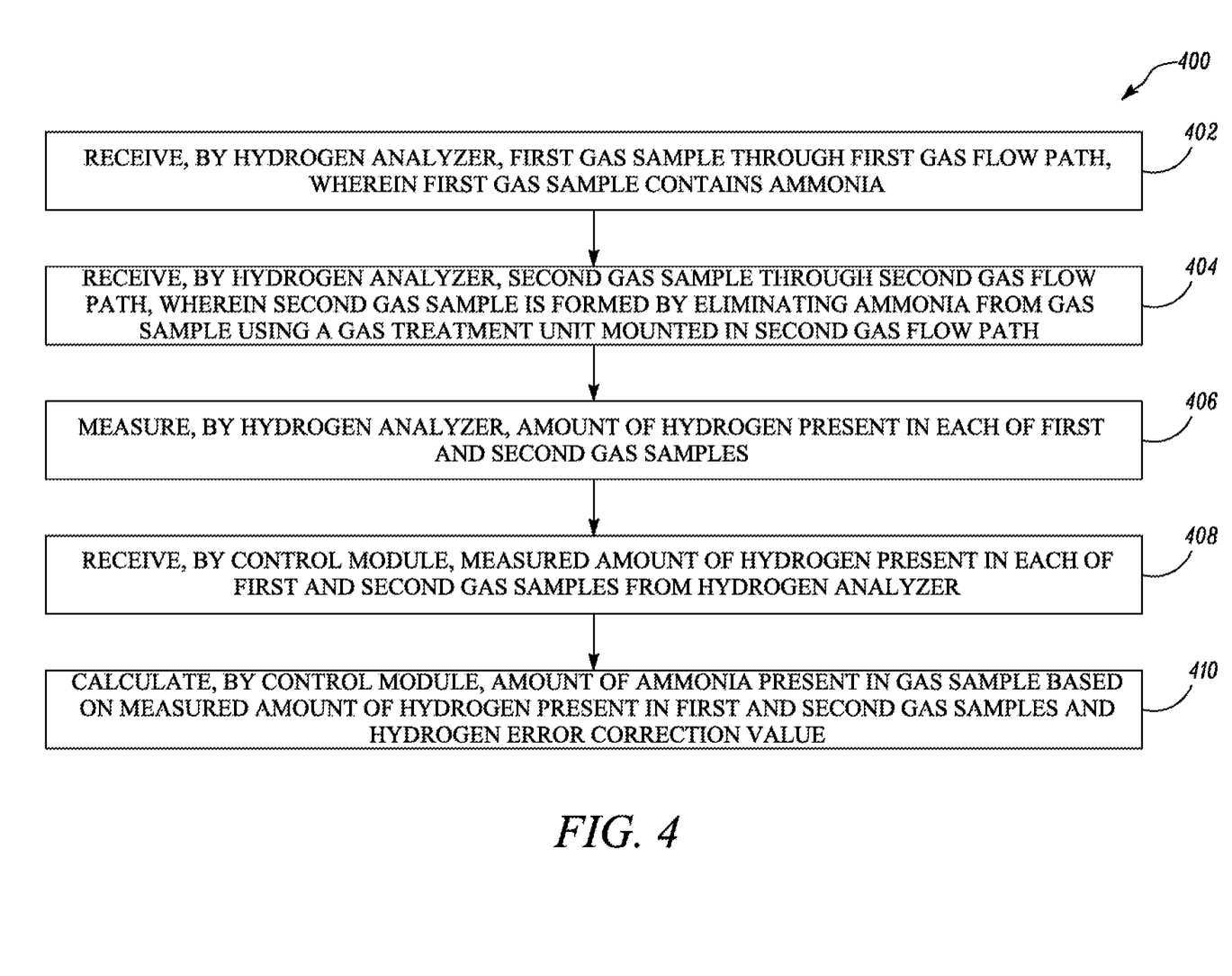
FIG. 4 is a flowchart for a method of calculating the amount of ammonia present in the gas sample.

The present disclosure relates to the system 104 and methods 300, 400 to calculate the amount of ammonia present in the gas sample, and more particularly, in the gas that is used in the gas nitriding process. The system 104 and methods 300, 400 make use of a low cost hydrogen analyzer 120 to measure the output signals for each of the first and second gas samples, which in turn are used to calculate the amount of ammonia in the gas sample. Thus, the system 104 and methods 300, 400 provide a cost effective solution for calculating the amount of ammonia present in the gas sample in order to control the gas nitriding process.

Additionally, the system 104 and methods 300, 400 used to calculate the amount of ammonia disclosed in this application are reliable and accurate as it involves an automated process for calculating the amount of ammonia and involves minimum human intervention. Further, the system 104 and methods 300, 400 described herein can be used in an industrial set-up as well as in lab environments for calculating the amount of ammonia. The system 104 can also be retrofitted to existing gas nitriding systems for calculating the amount of ammonia without making substantial changes or cost additions to the gas nitriding systems.

The method 300 for calculating the amount of ammonia present in the gas sample will now be described in detail with reference to FIG. 3. At step 302, the hydrogen analyzer 120 receives the first gas sample that contains ammonia. At step 304, the hydrogen analyzer 120 receives the second gas sample. The second gas sample is formed by eliminating ammonia from the gas sample. More particularly, the gas treatment unit 114 is mounted in the second gas flow path 112 to eliminate the ammonia from the gas sample. In one example, the gas treatment unit 114 includes the water bath 116 and the dryer 118. The dryer 118 is mounted downstream of the water bath 116 along the flow direction "F" of the second gas sample. In another example, the gas treatment unit 114 includes the catalyst.

Further, the first gas sample is received by the hydrogen analyzer 120 through the first gas flow path 110 and the second gas sample is received by the hydrogen analyzer 120 through the second gas flow path 112. Additionally, the valve arrangement 122 controls the receipt of the first gas sample and the second gas sample by the hydrogen analyzer 120. At step 306, the hydrogen analyzer 120 measures the output signals for each of the first and second gas samples.

At step 308, the amount of ammonia present in the gas sample is calculated based on the measured output signals the each of the first and second gas samples and the hydrogen error correction value. More particularly, the control module 124 receives the measured output signal for each of the first and second gas samples from the hydrogen analyzer 120 and calculates the amount of ammonia present in the gas sample. Furthermore, the control module 124 also determines the actual amount of hydrogen present in the gas sample, based on the measured output signal for the second gas sample.

Further, the hydrogen error correction value is calculated by measuring the output signal for the test gas sample at different concentrations of ammonia. Additionally, the number of coordinates "P1", "P2", "P3" is generated based on the measured output signal for the test gas sample corresponding to the respective known concentration of ammonia in the test gas sample. Based on the generated plurality of coordinates "P1", "P2", "P3", the curve "C" is created and the hydrogen error correction value is calculated by solving the equation of the curve "C".

The method 400 for calculating the amount of ammonia present in the gas sample will now be explained with reference to FIG. 4. At step 402, the hydrogen analyzer 120 receives the first gas sample containing ammonia through the first gas flow path 110. At step 404, the hydrogen analyzer 120 receives the second gas sample through the second gas how path 112. More particularly, the valve arrangement 122 controls a receipt of the first gas sample and the second gas sample by the hydrogen analyzer 120.

Further, the second gas sample is formed by eliminating ammonia from the gas sample using the gas treatment unit 114 mounted in the second gas flow path 112. In one example, the gas treatment unit 114 includes the water bath 116 and the dryer 118. The dryer 118 is mounted downstream of the water bath 116 along the flow direction "F" of the second gas sample. In another example, the gas treatment unit 114 includes the catalyst.

At step 406, the hydrogen analyzer 120 measures the output signal for each of the first and second gas samples. At step 408, control module 124 receives the measured output signals for each of the first and second gas samples from the hydrogen analyzer 120. At step 410, the control module 124 calculates the amount of ammonia present in the gas sample based on the measured output signals for each of the first and second gas samples and the hydrogen error correction value. Also, the control module 124 determines the actual amount of hydrogen present in the gas sample, based on the measured output signal for the second gas sample.

Further, the hydrogen error correction value is calculated by measuring the output signal for the test gas sample at different concentrations of ammonia. Additionally, the number of coordinates "P1", "P2", "P3" is generated based on the measured output signal for the test gas sample corresponding to the respective known concentration of ammonia in the test gas sample. Based on the generated plurality of coordinates "P1", "P2", "P3", the curve "C" is created and the hydrogen error correction value is calculated by solving the equation of the curve "C".

While aspects of the present disclosure have been particularly shown and described with reference to the embodiments above, it will be understood by those skilled in the art that various additional embodiments may be contemplated by the modification of the disclosed machines, systems and methods without departing from the spirit and scope of what is disclosed. Such embodiments should be understood to fall within the scope of the present disclosure as determined based upon the claims and any equivalents thereof.

The invention claimed is:

1. A method for calculating an amount of ammonia present in a gas, the method comprising:
   receiving a first sample of the gas within a hydrogen analyzer, wherein the first sample contains ammonia;
   generating a first output signal, by the hydrogen analyzer, indicative of a measured concentration of hydrogen in the first sample and an effect of ammonia on the hydrogen measurement;
   eliminating ammonia from a second sample of the gas;

receiving the second sample within the hydrogen analyzer after eliminating the ammonia from the second sample;

generating a second output signal, by the hydrogen analyzer, indicative of a concentration of hydrogen in the second sample; and calculating the amount of ammonia present in the gas based on a difference between the first output signal and the second output signal, and a hydrogen error correction value.

2. The method of claim 1, wherein the hydrogen error correction value is calculated by:

measuring a hydrogen concentration in a plurality of test gas samples, each test gas sample of the plurality of test gas samples having a unique and known concentration of ammonia;

generating a plurality of coordinates based on pairings of the hydrogen concentration and the ammonia concentration for each test gas sample in the plurality of test gas samples;

fitting a curve to the plurality of coordinates; and calculating the hydrogen error correction value by solving an equation that defines the curve.

3. The method of claim 1, wherein receiving the first sample and receiving the second sample are controlled by a valve arrangement.

4. The method of claim 1, wherein the first sample is received by the hydrogen analyzer through a first gas flow path, and the second sample is received by the hydrogen analyzer through a second gas flow path, the first gas flow path being different from the second gas flow path.

5. The method of claim 4, wherein the ammonia is eliminated from the second sample by a gas treatment unit included in the second gas flow path.

6. The method of claim 5, wherein the gas treatment unit includes a water bath and a dryer, the dryer being mounted downstream of the water bath along a flow direction through the second gas flow path.

7. The method of claim 5, wherein the gas treatment unit includes a catalyst.

8. The method of claim 1, further comprising receiving the first output signal and the second output signal within a control module.

9. The method of claim 8, further comprising determining, via the control module, an actual amount of hydrogen in the gas based on the second output signal.

10. A method for calculating an amount of ammonia present in a gas, the method comprising:

receiving, by a hydrogen analyzer, a first sample of the gas through a first gas flow path, wherein the first sample contains ammonia;

generating a first output signal, by the hydrogen analyzer, indicative of a measured concentration of hydrogen in the first sample and an effect of ammonia on the hydrogen measurement;

receiving a second sample of the gas within a gas treatment unit via a second gas flow path;

eliminating, by the gas treatment unit, ammonia from the second sample;

transferring the second sample from the gas treatment unit to the hydrogen analyzer after eliminating the ammonia from the second sample;

generating a second output signal, by the hydrogen analyzer, indicative of a concentration of hydrogen in the second sample;

receiving the first output signal and the second output signal within a control module; and calculating, by the control module, the amount of ammonia present in the gas based on a difference between the first output signal and the second output signal, and a hydrogen error correction value.

11. The method of claim 10, wherein the hydrogen error correction value is calculated by:

measuring a hydrogen concentration in a plurality of test gas samples, each test gas sample of the plurality of test gas samples having a unique and known concentration of ammonia;

generating a plurality of coordinates based on pairings of the hydrogen concentration and the ammonia concentration for each test gas sample in the plurality of test gas samples;

fitting a curve to the generated plurality of coordinates; and calculating the hydrogen error correction value by solving an equation that defines the curve.

12. The method of claim 11, further comprising determining, via the control module, an actual amount of hydrogen in the gas based on the second output signal.

13. The method of claim 10, wherein receiving the first sample within the hydrogen analyzer and receiving the second sample within the hydrogen analyzer are controlled by a valve arrangement.

14. The method of claim 10, wherein the gas treatment unit, includes a water bath and a dryer, the dryer being mounted downstream of the water bath along a flow direction through the second gas flow path.

15. The method of claim 10, wherein the gas treatment unit includes a catalyst.

16. A system for calculating an amount of ammonia present in a gas, the system comprising:

a hydrogen analyzer in selective fluid communication with a first gas flow path and a second gas flow path;

a gas treatment unit disposed along the second gas flow path and upstream of the hydrogen analyzer, the gas treatment unit being configured to eliminate ammonia from the gas as the gas flows through the gas treatment unit, wherein the hydrogen analyzer is configured to:

receive a first sample of the gas from the first gas flow path, the first sample containing ammonia, generate a first output signal indicative of a measured concentration of hydrogen in the first sample and an effect of ammonia on the hydrogen measurement, receive a second sample of the gas from the gas treatment unit along the second gas flow path after elimination of ammonia from the second sample via the gas treatment unit, and generate a second output signal indicative of a concentration of hydrogen in the second sample; and a control module communicably coupled with the hydrogen analyzer, wherein the control module is configured to:

receive the first output signal and the second output signal; and calculate the amount of ammonia present in the gas based on a difference between the first output signal and the second output signal, and a hydrogen error correction value.

17. The system of claim 16, wherein the hydrogen error correction value is calculated by:

measuring a hydrogen concentration in a plurality of test gas samples, each test gas sample of the plurality of test gas samples having a unique and known concentration of ammonia;

generating a plurality of coordinates based on pairings of the hydrogen concentration and the ammonia concentration for each test gas sample in the plurality of test gas samples;
fitting a curve to the generated plurality of coordinates; and
calculating the hydrogen error correction value by solving an equation that defines the curve.

18. The system of claim 16, wherein the gas treatment unit includes a water bath and a dryer, the dryer being mounted downstream of the water bath along a flow direction through the second gas flow path.

19. The system of claim 16, wherein the gas treatment unit includes a catalyst.

20. The system of claim 16, wherein the control module is further configured to determine an actual amount of hydrogen present in the second sample, based on the second output signal.

\* \* \* \* \*